US00PP20499P3

(12) United States Plant Patent
Corbett

(10) Patent No.: US PP20,499 P3
(45) Date of Patent: Nov. 24, 2009

(54) *PAULOWNIA* TREE NAMED 'ANAGENESIS TRIFOLIA'

(50) Latin Name: *Paulownia*
Varietal Denomination: Anagenesis Trifolia

(75) Inventor: Scot Corbett, Lenox, GA (US)

(73) Assignee: Anagenesis Trees Corporation, Voorhees, NJ (US)

( * ) Notice: Subject to any disclaimer, the term of this patent is extended or adjusted under 35 U.S.C. 154(b) by 0 days.

(21) Appl. No.: 12/009,422

(22) Filed: Jan. 18, 2008

(65) Prior Publication Data

US 2009/0188012 P1 Jul. 23, 2009

(51) Int. Cl.
*A01H 5/00* (2006.01)

(52) U.S. Cl. ..... Plt./216

(58) Field of Classification Search ..... Plt./186, Plt./216

See application file for complete search history.

*Primary Examiner*—Annette H Para

(74) *Attorney, Agent, or Firm*—Coats & Bennett, P.L.L.C.

(57) ABSTRACT

A new and distinct variety of *Paulownia* tree which combines the fast growing characteristics and drought tolerance of *Paulownia* Elongata, the straight growth characteristics of *Paulownia* Fortunei and the cold tolerance of *Paulownia* Catalpifolia. The *Paulownia* Anagenesis Trifolia is characterized by its flower color and its set of tri-pod branches evenly spaced around the tree trunk as they extend up the tree trunk at approximately 120 degree increments.

8 Drawing Sheets

Latin name of the genus and species of the plant claimed: *Paulownia* (genus), species not named.

Variety denomination: Anagenesis Trifolia.

BACKGROUND OF THE INVENTION

The present invention relates to a new and distinct form of *Paulownia* tree from the Scrophulariaceae—Figwort Family, botanically known as *Paulownia,* and referred to by the variety denomination Anagenesis Trifolia. This new *Paulownia* tree appears to be distinct from other known species in the genus *Paulownia.* This new *Paulownia* variety produces a significant increase in fiber volume making it ideal for biomass production.

*Paulownia* trees are native to mainland China and Southeast Asia. They are easily identified by their large semi-heart shaped leaves and clusters of cascading mauve to white flowers that appear in early spring before the trees go into leaf. *Paulownia* has been successfully grown in the United States for more than 100 years. However, commercial plantations have only been in existence since the late 1980s. In the Southeast United States, *Paulownia* often serves as substitute for pine, poplar and other local hardwoods. The *Paulownia* tree is relatively fast growing and therefore has the ability to regenerate after harvest, making it ideal as a renewable source for timber and fiber for biomass production. The wood is light weight yet strong and useful for plywood, furniture, veneer, oriented strand board, paper making and log homes.

Significant research and development has been carried out to improve the genus and to develop new and distinct varieties that will grow in colder growing zones yet still demonstrate fast growth and drought tolerance. The *Paulownia* Anagenesis Trifolia is a hybrid resulting from crossing selected offspring of *Paulownia* Elongata and *Paulownia* Fortunei with *Paulownia* Catalpifolia. This variety has the fast growing characteristics and drought tolerance of *Paulownia* Elongata, the straight growth characteristics of *Paulownia* Fortunei and the cold tolerance of *Paulownia* Catalpifolia.

The first act of asexual reproduction of the new form was accomplished in Lenox Ga. The clones of the new form are identical to the original plant in all distinguishing characteristics.

SUMMARY

The present invention, *Paulownia* Anagenesis Trifolia, is a new and distinct variety of the genus *Paulownia* which combines the fast growing characteristics and drought tolerance of *Paulownia* Elongata, the straight growth characteristics of *Paulownia* Fortunei and the cold tolerance of *Paulownia* Catalpifolia. *Paulownia* Anagenesis Trifolia can mature to a height of 30–35 meters and grow as far north as zone 5A on the USDA plant hardiness zone. This variety can withstand average annual minimum temperature between −15 to −20 F. and can be cultivated in areas that have as little as 6–12 inches of rain fall per annum.

The *Paulownia* Anagenesis Trifolia also distinguishes itself from other *Paulownia* varieties with its sets of three branches evenly spaced around the tree trunk at approximately 120 degree increments. The additional fiber volume produced as a result of the tripod type branch network increases the fiber production of the tree 20% to 30% annually.

BRIEF DESCRIPTION OF THE DRAWINGS

The accompanying photographs show specimens of the new variety, with their foliage and flowers in different stages of development.

DETAILED DESCRIPTION OF THE PLANT

In the following description, color references are made to The Royal Horticultural Society (R.H.S.) Colour Chart, (2001) Edition. Where dimensions, sizes, colors and other characteristics are given, it is to be understood that such characteristics are approximations of averages set forth as accurately as practicable. The descriptions reported herein, unless otherwise stated, are from 6 month old and 1 year old specimens grown at a nursery and field plantings in Lenox, Ga.

Botanical classification: *Paulownia* referred to by the variety denomination Anagenesis Trioflia.

Parentage: The ovary of *Paulownia* Elongata was fertilized with the pollen of *Paulownia* Fortunei to produce initial offspring. The ovary of this offspring was fertilized with the pollen of *Paulownia* Catalpifolia to produce the new and distinct variety of *Paulownia.*

Propagation: The *Paulownia* Anagenesis Trifolia has been asexually reproduced in Lennox, Ga. and all clones are identical to the original plant in all distinguishing characteristics. The seeds from *Paulownia* Anagenesis Trifolia were germinated and grown into seedlings in a greenhouse. Micro-propagation and multiplication of the original seedlings was performed by tissue culture. Rooted tissue cultures were potted in standard potting mix and grown in a greenhouse for 45 days before transplanting to the field.

Figure 8:
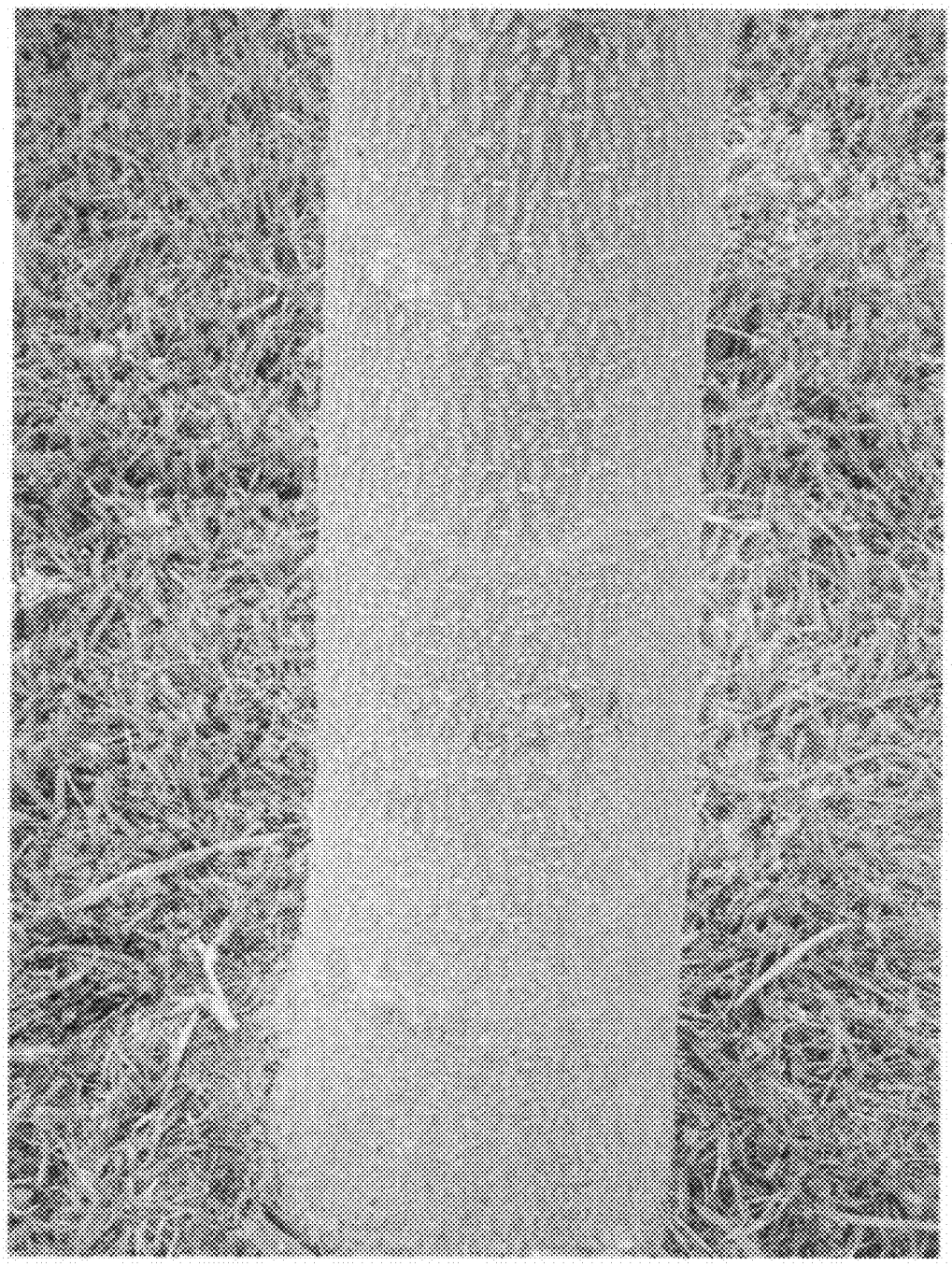
FIG. 8. Trunk of a 2-year old *Paulownia* Anagenesis Trifolia grown in Lenox, Ga.

Plant description: The *Paulownia* Anagenesis Trifolia is a deciduous hardwood tree that is expected to matures to a height of 30–35 meters in 15–20 years. The mature tree is expected to have a full umbrella like crown that measures up to 15 meters across. The 1-year old *Paulownia* Anagenesis Trifolia has a height of approximately 7 meters and measures up to 4 meters across. A mature *Paulownia* Anagenesis Trifolia of between 15–20 years is expected to have a trunk diameter that will reach between 800 mm to 900 mm. The 1-year old *Paulownia* Anagenesis Trifolia has a trunk DBH (diameter at breast height) of approximately 75 mm. The mature tree has a trunk shape that is terete with bark that is smooth to textured. The bark has a black grey/grey color as referenced by the RHS Black Grey group 202C to the RHS Grey group 201D. FIG. 8 shows an example of the trunk of a 2-year old *Paulownia* Anagenesis Trifolia.

Foliage: Infant leaves, between 6 months old and 1-year old, reach approximately 20 to 30 inches in diameter, are cordate in shape, and have a green color as referenced by the RHS Green group 139A to 141B with visible hirsute veins which have a yellow color as referenced by the RHS Yellow group 2D. Mature leaves are much smaller, approximately 8 to 12 inches in diameter, cordate in shape with visible veins having a smooth margin and a hirsute texture.

Fruits: The bi-valve fruit capsules are ovate in shape and form during the months of April and May. The fruit capsules vary in color within the RHS Grey Brown group 199C to N199D. The fruit capsules mature during September and October and are approximately 1.5 inches in length. Hundreds of wing type minute seeds are produced in each capsule.

Figure 6:
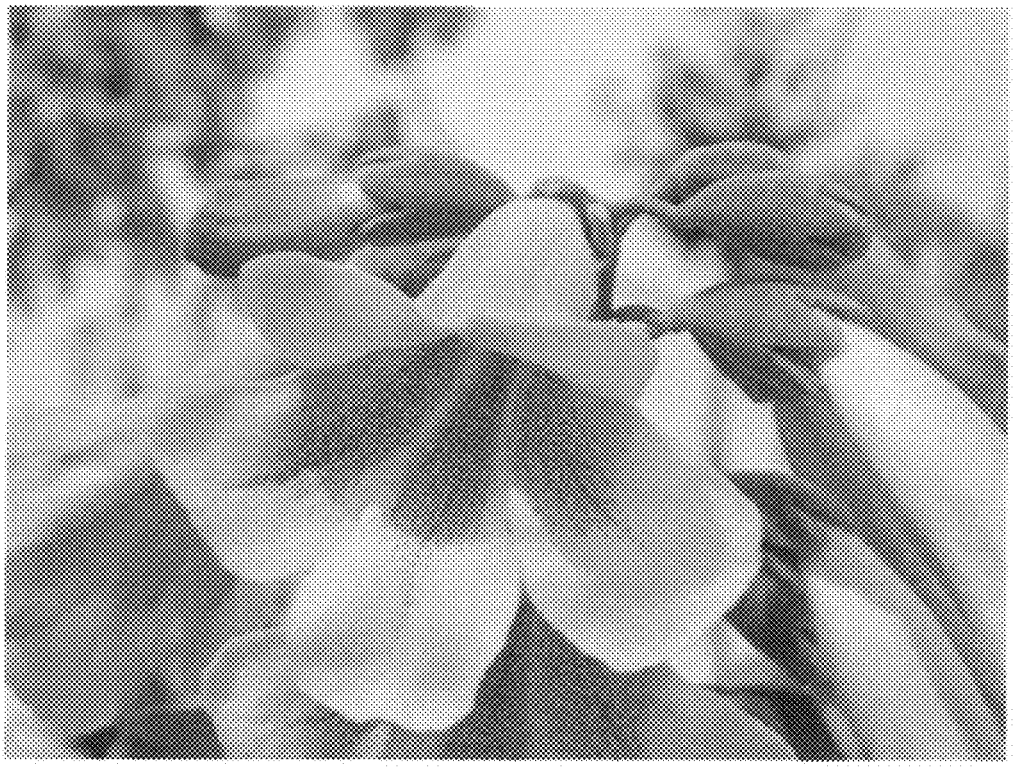
FIG. 6. A flower from the *Paulownia* Elongata, a parent of the *Paulownia* Anagenesis Trifolia grown in Lenox, Ga.
Figure 7:
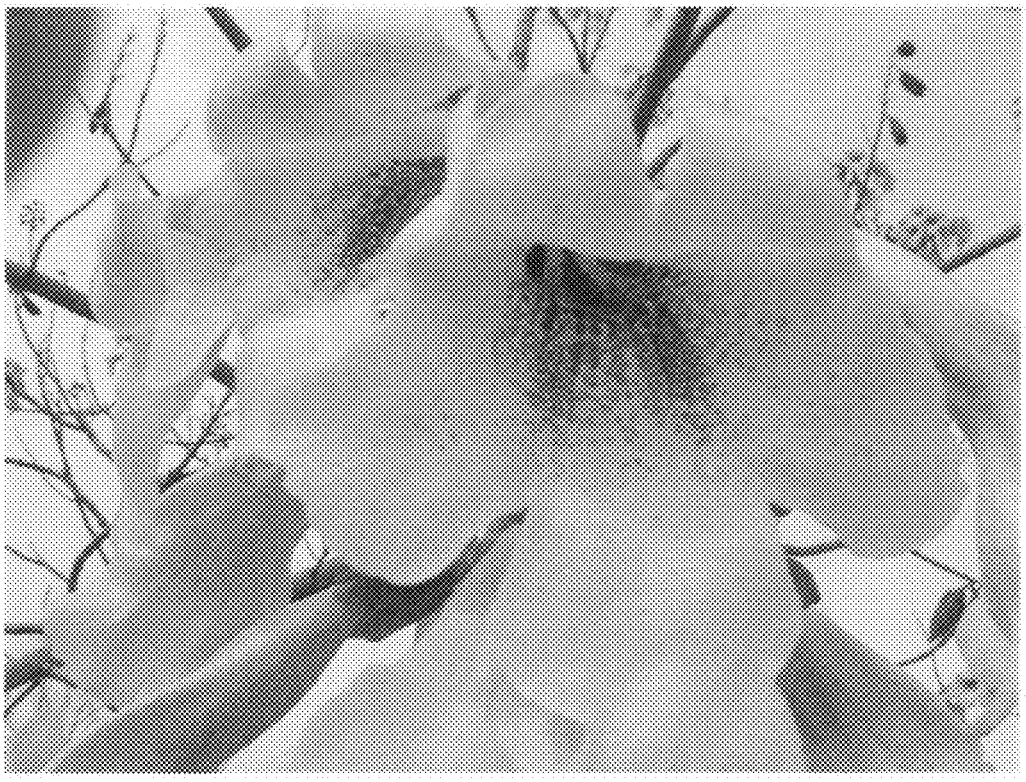
FIG. 7. A flower from the *Paulownia* Catalpifolia, a parent of the *Paulownia* Anagenesis Trifolia grown in Lenox, Ga.

Flowers: *Paulownia* Anagenesis Trifolia typically exhibits 6 to 9 cyme inflorescence, approximately 2 inches in length. The flower buds form in autumn and are light green in color. Flowers emerge during March and April displaying a deep violet/blue color as referenced by the RHS Violet Blue group 97A to the RHS White group 155A. The calyx is fleshy with 5 hirsute elongated lobes and a companulate corolla tube. The ovary is bilocular and the pistil is the same length as the stamens. There are 4 didynamous stamens which are about half as long as the corolla. There are generally two yellow stripes as referenced by the RHS Yellow group 3-B, running the length of the corolla. The color of the flowers will vary depending upon soil type, soil fertility and soil pH. The flower color of the *Paulownia* Anagenesis Trifolia differs from its parents and all other *Paulownia* varieties. FIGS. 6 and 7 show the flowers from the *Paulownia* Elongata and *Paulownia* Catalpifolia, respectively, both of which are parents of the *Paulownia* Anagenesis Trifolia.

Figure 1:
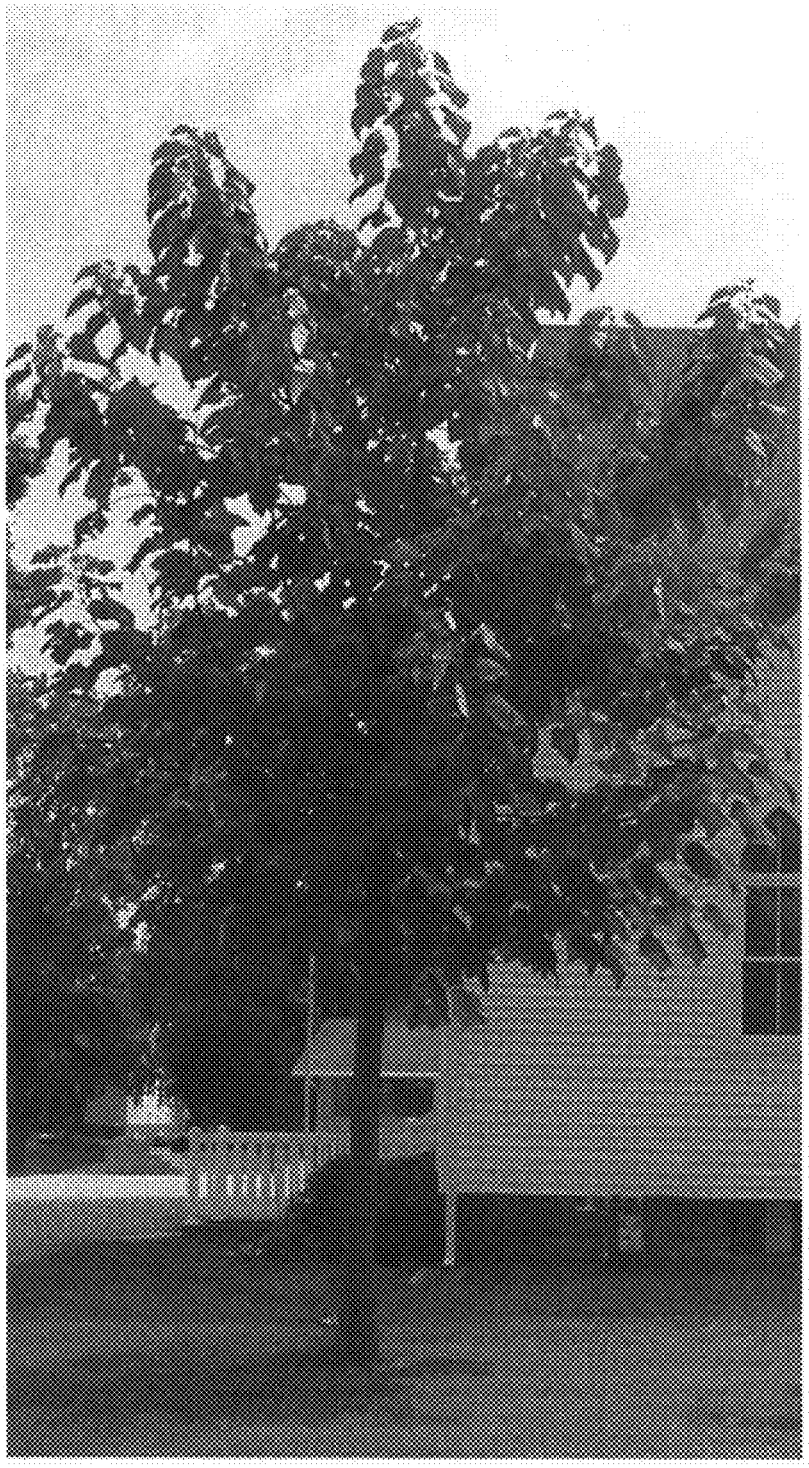
FIG. 1. A *Paulownia* Anagenesis Trifolia tree at approximately 1 year in age grown in Lenox Ga.
Figure 2:
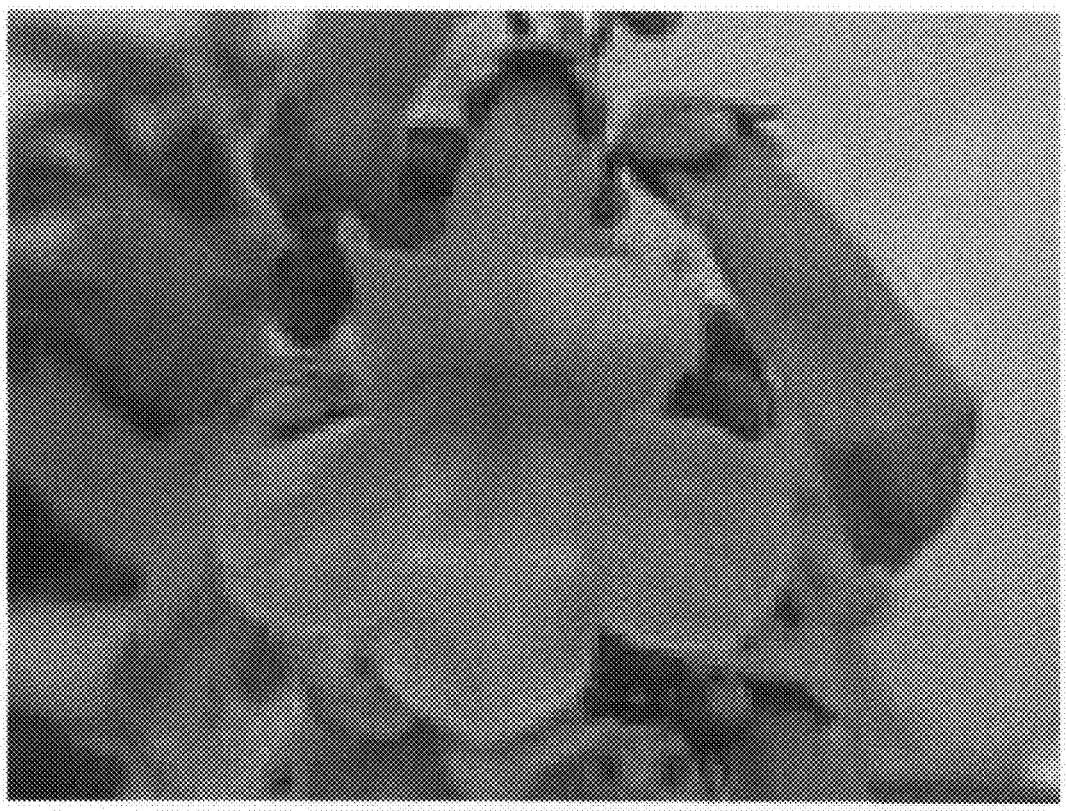
FIG. 2. A flower the *Paulownia* Anagenesis Trifolia from 1 year old tree grown in Lenox Ga.
Figure 3:
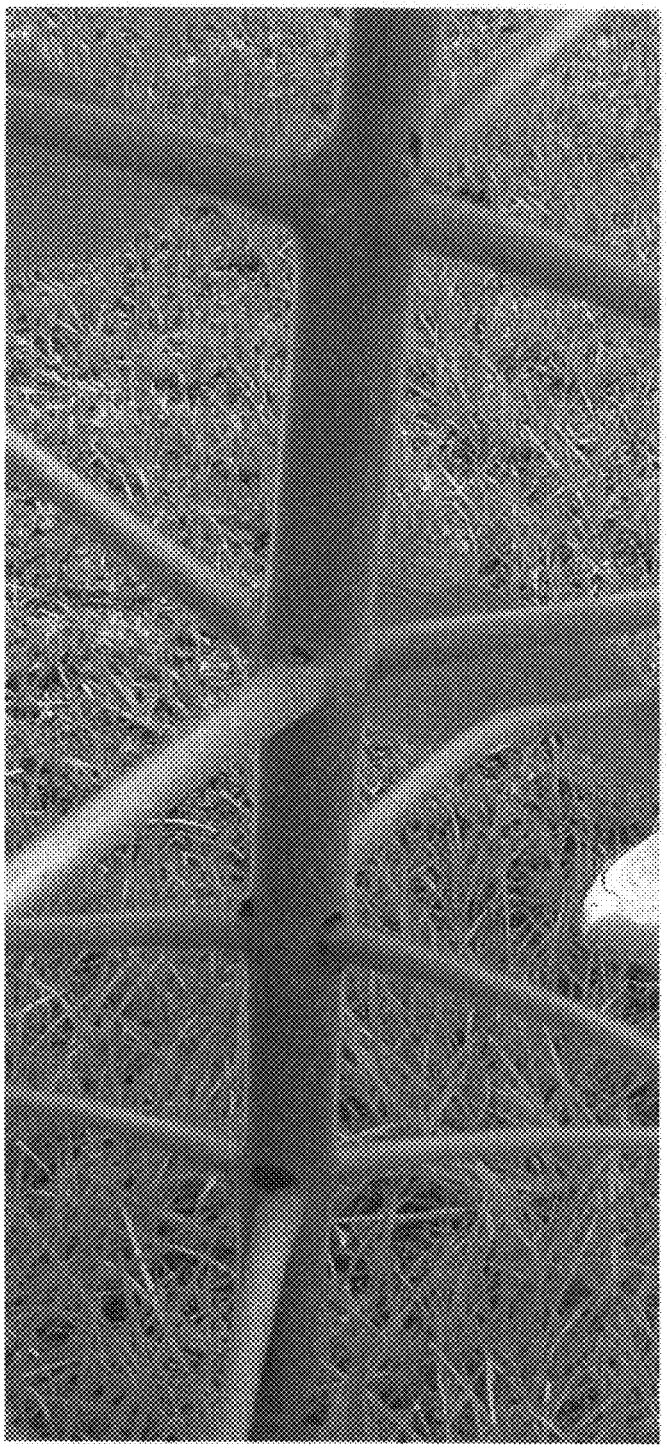
FIG. 3. Branches of a young *Paulownia* Anagenesis Trifolia 6 month old grown in Lenox, Ga.
Figure 4:
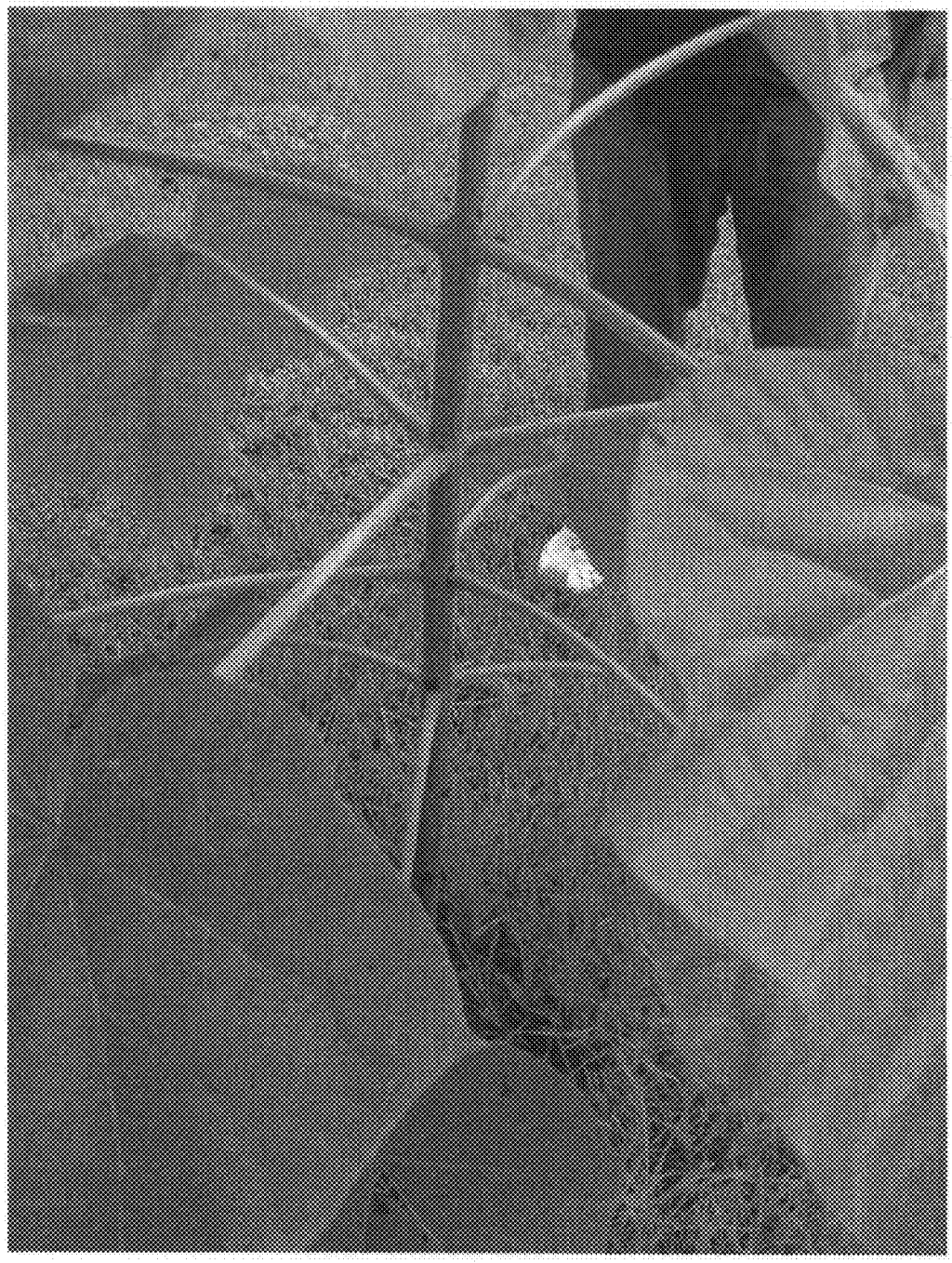
FIG. 4. Foliage of a young *Paulownia* Anagenesis Trifolia approximately 6 months old grown in Lenox Ga.
Figure 5:
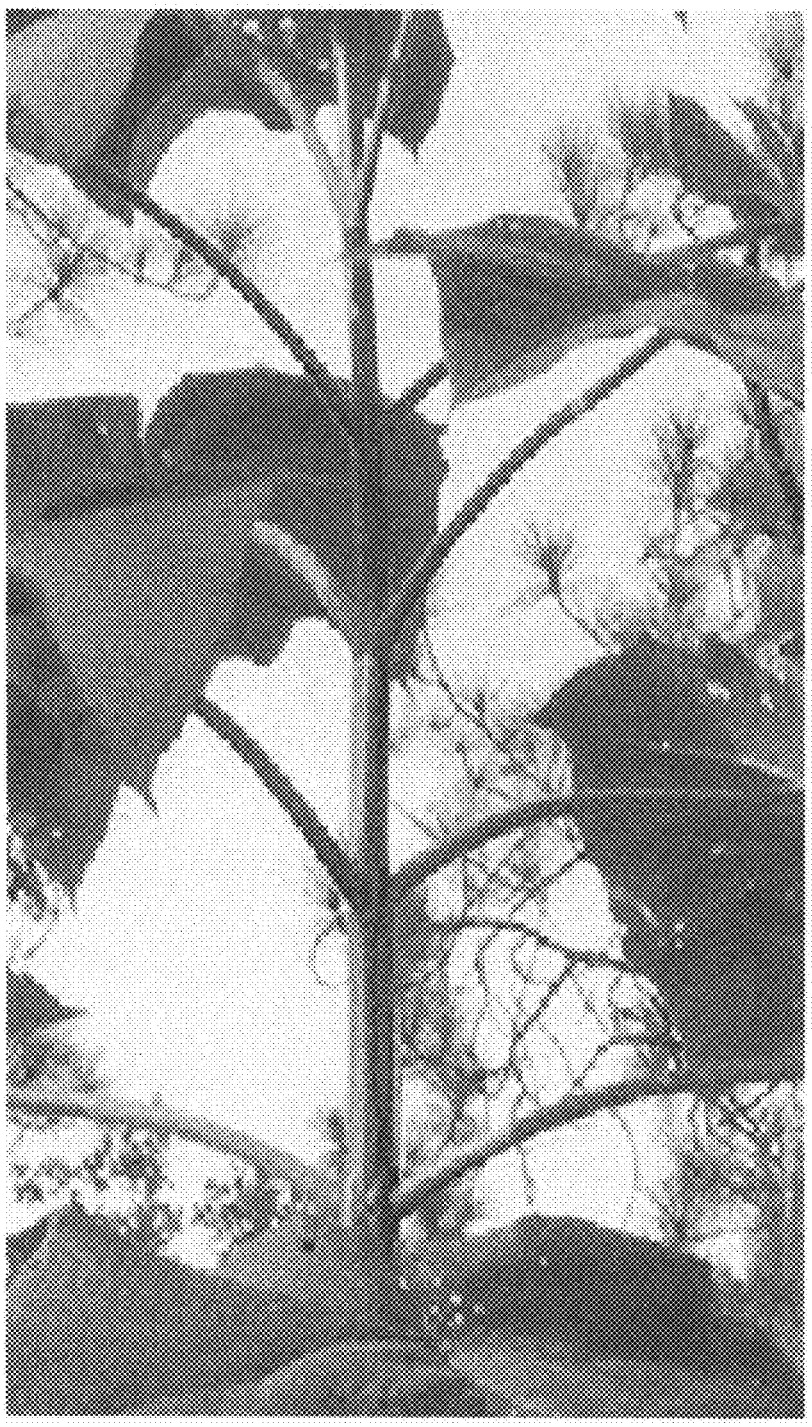
FIG. 5. Typical *Paulownia* branch net work as is apparent on all other *Paulownia* Varieties. This photograph is of a 2 year old *Paulownia* Elongata grown in Lenox Ga.

Form and branching: The *Paulownia* Anagenesis Trifolia has a distinct difference in branch characteristics from its parents and all other *Paulownia* trees. Generally, *Paulownia* tree branches form in pairs along the trunk that grow 180 degrees opposite each other. See FIG. 5. The *Paulownia* Anagenesis Trifolia however, has a tri-pod or triplet branch network. In particular, the tree has sets of three branches evenly spaced around the circumference of the tree trunk at approximately 120 degree increments. See FIG. 3. The additional fiber volume produced as a result of the tripod type branch network increases the fiber production of the tree 20% to 30% annually.

Tolerance: *Paulownia* Anagenesis Trifolia is more cold tolerant than most other *Paulownia* varieties. Most *Paulownia* trees can be cultivated as far north as zone 6B and can withstand an average annual minimum temperature of 0 to −5 F. However, the *Paulownia* Anagenesis Trifolia has been successfully grown as far north as USDA plant hardiness zone 5A and can withstand an average annual minimum temperature of −15 to −20 F. This new variety is drought tolerant and can be cultivated in areas that have as little as 6 to 12 inches of rain fall per annum.

What is claimed is:

1. A new and distinct variety of *Paulownia* tree as shown and described, characterized by its flower color, fast growing characteristics, cold and drought tolerance, and tri-pod type branch network resulting in increased fiber production.

* * * * *